US007802503B2

(12) United States Patent
Couvillion et al.

(10) Patent No.: US 7,802,503 B2
(45) Date of Patent: Sep. 28, 2010

(54) METHOD AND APPARATUS FOR PREPARING BONE GRAFTS, INCLUDING GRAFTS FOR LUMBAR/THORACIC INTERBODY FUSION

(76) Inventors: Roy J. Couvillion, 1005 La Neuville Rd., Lafayette, LA (US) 70508; John E. Cobb, 1211 Coolidge Blvd., Lafayette, LA (US) 70503

( * ) Notice: Subject to any disclaimer, the term of this patent is extended or adjusted under 35 U.S.C. 154(b) by 530 days.

(21) Appl. No.: 11/487,102

(22) Filed: Jul. 14, 2006

(65) Prior Publication Data

US 2008/0011136 A1 Jan. 17, 2008

(51) Int. Cl.
*A61B 17/32* (2006.01)

(52) U.S. Cl. ............................... 83/39; 83/454; 83/459; 83/762; 606/87; 269/87.2

(58) Field of Classification Search ................... 83/452, 83/454, 456, 459, 465, 762–767; 606/87; 269/87, 87.2, 43, 45
See application file for complete search history.

(56) References Cited

U.S. PATENT DOCUMENTS

| | | | | | |
|---|---|---|---|---|---|
| 1,426,026 | A | * | 8/1922 | Webster | 72/474 |
| 1,636,181 | A | * | 7/1927 | Glassey | 269/212 |
| 2,003,619 | A | * | 6/1935 | Williamson | 269/87.2 |
| 2,441,379 | A | * | 5/1948 | Zimmermann | 269/87 |
| 2,613,714 | A | * | 10/1952 | Miller | 83/762 |
| 3,768,797 | A | * | 10/1973 | Kartasuk et al. | 269/283 |
| 4,133,519 | A | * | 1/1979 | Shin et al. | 269/247 |
| 4,960,269 | A | * | 10/1990 | Fong | 269/87.2 |
| 5,042,983 | A | | 8/1991 | Rayhack | |
| 5,145,157 | A | * | 9/1992 | Polk | 269/266 |
| 5,176,685 | A | | 1/1993 | Rayhack | |
| 5,817,097 | A | | 10/1998 | Howard et al. | |
| 6,152,435 | A | * | 11/2000 | Snell | 269/43 |
| 6,648,894 | B2 | * | 11/2003 | Abdelgany et al. | 606/79 |
| 6,676,662 | B1 | | 1/2004 | Bagga et al. | |
| 7,073,783 | B1 | * | 7/2006 | Somerville et al. | 269/25 |
| 2002/0138078 | A1 | | 9/2002 | Chappuis | |
| 2004/0034360 | A1 | * | 2/2004 | Dalton | 606/87 |
| 2004/0034361 | A1 | | 2/2004 | Dalton | |
| 2004/0034362 | A1 | | 2/2004 | Abdelgany et al. | |
| 2004/0220578 | A1 | | 11/2004 | Bagga et al. | |

OTHER PUBLICATIONS

Albee, Fred H. "Bone Surgery with Machine Tools". Apr. 1936. Scientific American.*

* cited by examiner

*Primary Examiner*—Boyer D. Ashley
*Assistant Examiner*—Edward Landrum
(74) *Attorney, Agent, or Firm*—Ted M. Anthony

(57) ABSTRACT

A base having a substantially planar surface, an upright support member and a blade guide having a serrated surface that can be adjustably positioned along the planar surface. The blade guide is biased toward an opposing serrated plate member to securely hold a section of donor bone, and locked in place using an adjustable lever-cam linkage.

2 Claims, 10 Drawing Sheets

METHOD AND APPARATUS FOR PREPARING BONE GRAFTS, INCLUDING GRAFTS FOR LUMBAR/THORACIC INTERBODY FUSION

BACKGROUND OF THE INVENTION

1. Field of the Invention

The present invention relates to a method and apparatus for preparing bone grafts for use in the repair, replacement, and/or augmentation of various portions of animal or human skeletal systems. More particularly, the present invention relates to prepared bone grafts, guides for forming bone grafts and methods for forming bone grafts.

2. Brief Description of the Prior Art

Several procedures involve the use and implantation of bone into an animal or human body. Generally, benefits of implanted bone include, but are not limited to, providing support, promoting healing, filling cavities, separating or spacing bony elements such as vertebral bodies, promoting fusion, and stabilizing the site of fractures.

Although the use of bone grafts is not limited to the spine, bone grafts are frequently implanted during certain surgical procedures to promote surgical decompression and/or stabilization of the spine. Such procedures include, but are not necessarily limited to, spinal discectomy with fusion and postcorpectomy reconstruction. In such procedures, autogenic, allogenic or xenogenic bone or synthetic material can be used to provide structural support in voids where diseased or damaged tissue or bone has been removed from the spine.

During such procedures, it is often critically important that the size and geometry of the implanted bone be consistent with the void into which said implanted bone is ultimately introduced. Put another way, the success of such procedures frequently depend, at least in large part, on the degree to which the size and geometry of the an implanted bone section matches the void that will receive said bone section.

Practitioners generally have a number of different options available when choosing inter-body fusion implants. Such implants can basically be segregated into two groups: mechanical devices and actual bone. When using actual bone implants, practitioners can utilize pre-processed bone grafts that are currently available in a number of different configurations and geometries. Alternatively, practitioners can prepare an implant graft intra-operatively using a section of donor bone. Autogenic grafts, by their very nature, must be prepared intra-operatively.

Some practitioners prefer intra-operative graft preparation. Even when measurements translated from pre-operative non-invasive imagery are used to determine appropriate graft geometry, intra-operative measurement is still required to ensure proper fit of a particular graft. Intra-operative bone graft preparation allows a surgeon to customize an implant to fit a particular application. Some practitioners will even modify pre-processed bone grafts prior to insertion.

Alternatively, a section of a bone can be taken directly from the patient receiving the implant. In such cases, a "donor" bone (known as an "autograft") is harvested from another part of a patient's body and used as in implant during the surgical procedure. However, the autograft is frequently longer and/or shaped differently than the required bone implant. Thus, the donor bone often must be cut to precise lengths and/or at precise angles.

When using a patient's donor bone, it is frequently necessary to form required bone implant sections directly in the intra-operative environment such as the operating room itself. Moreover, multiple graft implants are frequently required. To minimize trauma associated with autographic bone harvesting, it is typically advantageous to form multiple graft sections from the same donor bone.

Thus, there is a need for a simple, inexpensive and effective method and apparatus for the manufacture of bone implants directly in an intra-operative environment. The subject apparatus should allow a surgeon to produce, and thereafter faithfully reproduce, grafts with a high degree of precision. The subject apparatus should be robust, durable, easy to use, and consistent with surgical environment(s) and compatible with existing cutting tools.

SUMMARY OF THE PRESENT INVENTION

The present invention is a method and apparatus for forming bone grafts from autogenic, allogenic or xenogenic bone. The device of the present invention can be used in virtually any environment, including intra-operative environments such operating rooms and/or other facilities used for performing surgical procedures. The present invention can be beneficially sized to accommodate different sizes and shapes of donor bones, and can be easily cleaned and/or autoclaved for repeated use. Further, the present invention permits formation of bone grafts by a single operator, including an operator having compromised dexterity and/or hand strength. Nonetheless, the present invention also allows an assistant or secondary operator to aid in its use by providing lighting, irrigation and the like.

In one preferred embodiment, the present invention comprises a base having a substantially planar surface. For most applications, said base and substantially planar surface have a substantially horizontal orientation. An upright member having an opening is disposed at one end of said base. At least one slotted track is formed on the planar surface of said base.

A plate member is mounted vertically under said base, and forms a curved, serrated surface that protrudes from the opening in said upright member. In the preferred embodiment, such serrated surface has a generally concave shape and is beneficially oriented normal to the longitudinal axis of said upright member. In the preferred embodiment, such vertical plate member also forms a tab which extends above the substantially planar surface of such base.

A moveable blade guide is slidably received within said at least one track of said base. Said blade guide can travel along said substantially planar base within said at least one track and can be selectively positioned along said planar surface of said base. Said blade guide further has a bone holder and a plurality of slots extending through said bone holder. In the preferred embodiment, said bone holder further defines a curved surface having a shape and configuration that can accommodate the outer (generally cylindrical) surface of a donor bone. A plurality of teeth or serrations is ideally disposed on such curved surface of said bone holder.

A section of donor bone can be placed on the serrated surface of the vertical plate member protruding from the opening in the upright member of the base. Thereafter, said blade guide can be moved within said at least one track until the blade guide is secured in a desired position against such donor bone. In this configuration, the donor bone is secured in compression between the serrated surface of the vertical plate member and the and bone holder of the blade guide. Once a donor bone is secured in place, precision cuts can be made to said donor bone in order to prepare bone grafts having desired shapes and sizes.

In the preferred embodiment, two opposing serrated surfaces are used to secure a section of donor bone in place for cutting operations. The serrated surface of the vertical plate member is beneficially oriented normal to the longitudinal axis of a donor bone to be held by such serrated surface. In this embodiment, the opposing surface used to secure a section of bone is a serrated extension located on the bone holder of a blade guide, wherein said serrated extension is beneficially centered between slots in such blade guide. The blade guide is biased toward said serrated surface of the vertical plate member (and any section of donor bone resting on said surface) and locked in place using an adjustable lever-cam linkage. The apparatus allows for differences in size and geometry of a donor bone, as well as compression forces to be applied to such donor bone, using a movable yoke as part of such linkage.

In one embodiment of the invention, a bone graft having parallel faces can be prepared. Slots formed in the blade guide allow a cutting device, such as a saggital saw blade well known in the art, to move freely within a plane of radical oscillation. Said slots can guide the cutting edge of such a blade through a donor bone within the desired plane. In this embodiment, such slots are situated at varied but fixed spacing intervals and at normal angles relative to the longitudinal axis of said donor bone. Moreover, because multiple aligned slots are formed in the blade guide, two faces of a bone graft can be completed without repositioning a donor bone.

In another aspect of the invention, a bone graft with convergent oblique faces can be prepared. An alternative blade-guide having slots formed at converging oblique angles relative to the longitudinal axis of a donor bone can be used. Because multiple aligned slots are formed in the blade guide and base, two faces of a bone graft can be completed without repositioning a donor bone.

In yet another embodiment of the invention, a graft combining right and oblique faces can be prepared. An alternative blade-guide having slots cut at both normal and oblique angles relative to the longitudinal axis of a donor bone can be used. Again, because multiple aligned slots are formed in the blade guide and base, two faces of a bone graft can be completed without repositioning a donor bone.

The device of the present invention is robust and can be used in virtually any environment, including intra-operative environments such as those operating rooms and/or other facilities used for performing surgical procedures. The components of the present invention can be easily reconfigured as desired to fit different types of donor bones, and can be easily cleaned and/or autoclaved for repeat use.

DETAILED DESCRIPTION OF A PREFERRED EMBODIMENT OF THE INVENTION

Figure 1:
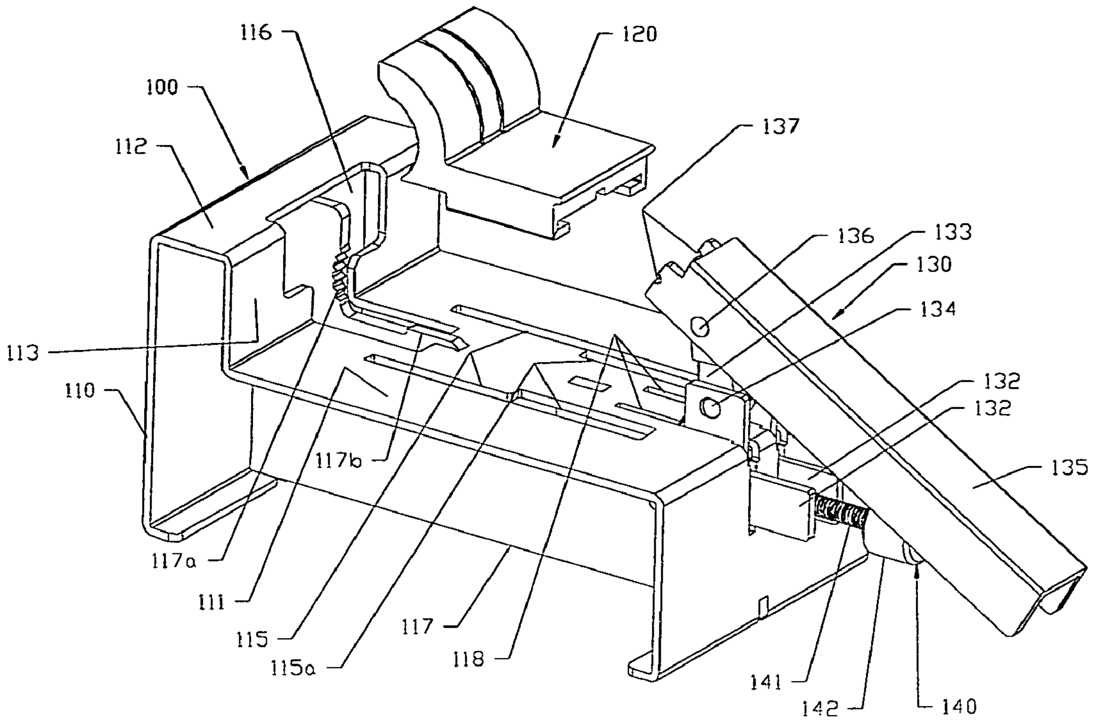
FIG. 1 depicts a partially exploded perspective view of the cutting apparatus of the present invention.

Referring to the drawings, FIG. 1 depicts cutting apparatus 100 of the present invention providing a robust mechanism for securing a section of donor bone used to prepare bone grafts. Base 110 comprises substantially planar surface 111. In most applications, substantially planar surface 111 is situated in a substantially horizontal orientation. Elongate upright member 112 extends along one side of said base 110. In the preferred embodiment, base 110 is formed from sheet stock or other similar material so that upright member 112 is not solid. Upright member defines substantially vertical surface 113. Tracks 115 are situated along planar surface 111 of base 110, and are oriented in a direction that is substantially perpendicular to the longitudinal axis of upright member 112. In the preferred embodiment, tracks 115 have wider openings 115*a* opposite upright member 112. Blade guide 120 can be slidably disposed within tracks 115.

Still referring to FIG. 1, opening 116 is formed in substantially vertical surface 113 of upright member 112. Plate member 117, which is partially mounted under base 110, defines serrated surface 117*a*. In the preferred embodiment, serrated surface 117*a* has a generally concave surface and is beneficially oriented normal to the longitudinal axis of upright member 112 (and a donor bone section to be cut to form a graft). Plate member 117 also defines centering tab 117*b*. The lateral position of blade guide 120 is limited by centering tab 117*b*.

As described in detail below, cam lever linkage 130 is used to bias blade guide toward serrated surface 117*a* (and any donor bone section situated thereon). Cam lever linkage 130 comprises yoke 131; said yoke 131 is slidably disposed within slotted tracks 118 of base 110 and has lateral extension members 132. Pivot arm 133 is pivotally mounted to yoke 131 via pivot pin 134 and to lever arm 135 via pivot pin 136. Lever arm 135 has slot 137 along its forward edge closest to serrated surface 117*a*. Biasing bolt 140 comprises threaded section 141 and head 142. Head 142 of biasing bolt 140 is wider than the gap formed between lateral extension members 132 of yoke 131. Threaded section 141 of biasing bolt 140 is received within a threaded bore in base 110 (not shown in FIG. 15).

Figure 2:
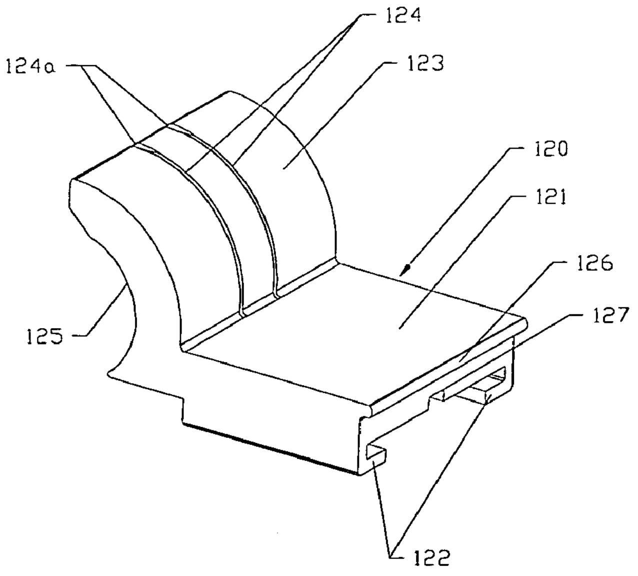
FIG. 2 depicts an overhead perspective view of a blade guide of the cutting apparatus of the present invention.

Referring to FIG. 2, blade guide 120 comprises body section 121 and bone holder 123. Opposing L-shaped track mounts 122 are disposed along the base of body section 121. In the preferred embodiment, bone holder 123 defines curved inner surface 125 having a geometry that can accommodate the outer (generally cylindrical) surface of a donor bone. A plurality of slots 124 is formed in bone holder 123. In FIG. 2, slots 124 are depicted as being in parallel orientation relative to one another. However, it is to be observed that slots 124 need not be parallel, and can be oriented at any number of beneficial angles relative to one another. In the preferred embodiment, said slots have wider, tapered areas 124a near the leading edge of said blade guide 120. Lateral extension 126 protrudes from blade guide 120 on the opposite side of blade guide 120 from bone holder 123. Centering groove 127 mates with centering tab 117*b* (shown on FIG. 1).

Figure 3:
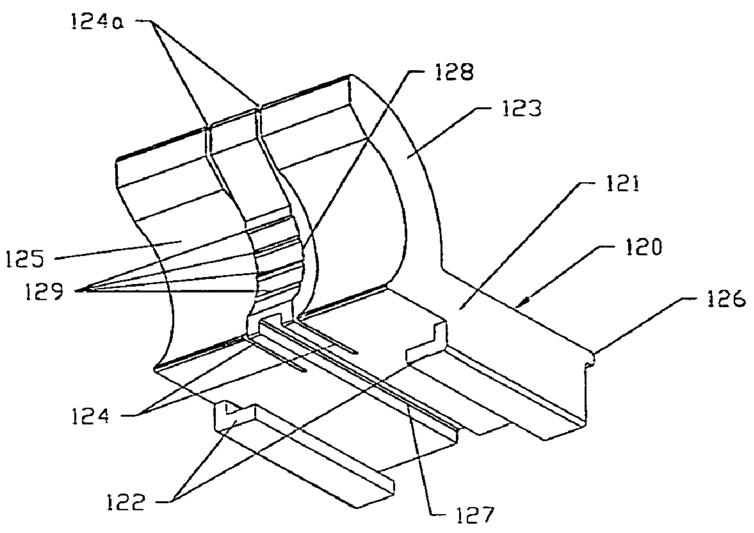
FIG. 3 depicts a lower perspective view of a blade guide of the cutting apparatus of the present invention.

FIG. 3 depicts an alternative perspective view of blade guide 120. Referring to FIG. 3, blade guide 120 comprises body section 121 and bone holder 123. Opposing track mounts 122 are disposed along the base of body section 121. In the preferred embodiment, bone holder 123 defines curved inner surface 125 having a geometry that can accommodate the outer (generally cylindrical) surface of a donor bone. A plurality of slots 124 are formed in bone holder 123. In the preferred embodiment, said slots 124 partially extend into body section 121 and have wider, tapered areas 124*a* near the leading edge of blade guide 120. Lateral extension 126 protrudes from blade guide 120 on the opposite side of blade guide 120 from bone holder 123. Toothed protrusion 128 extends from curved inner surface 125 of bone holder 123. In the preferred embodiment, toothed protrusion 128 is beneficially centered between slots 124 in bone holder 123.

Figure 4:
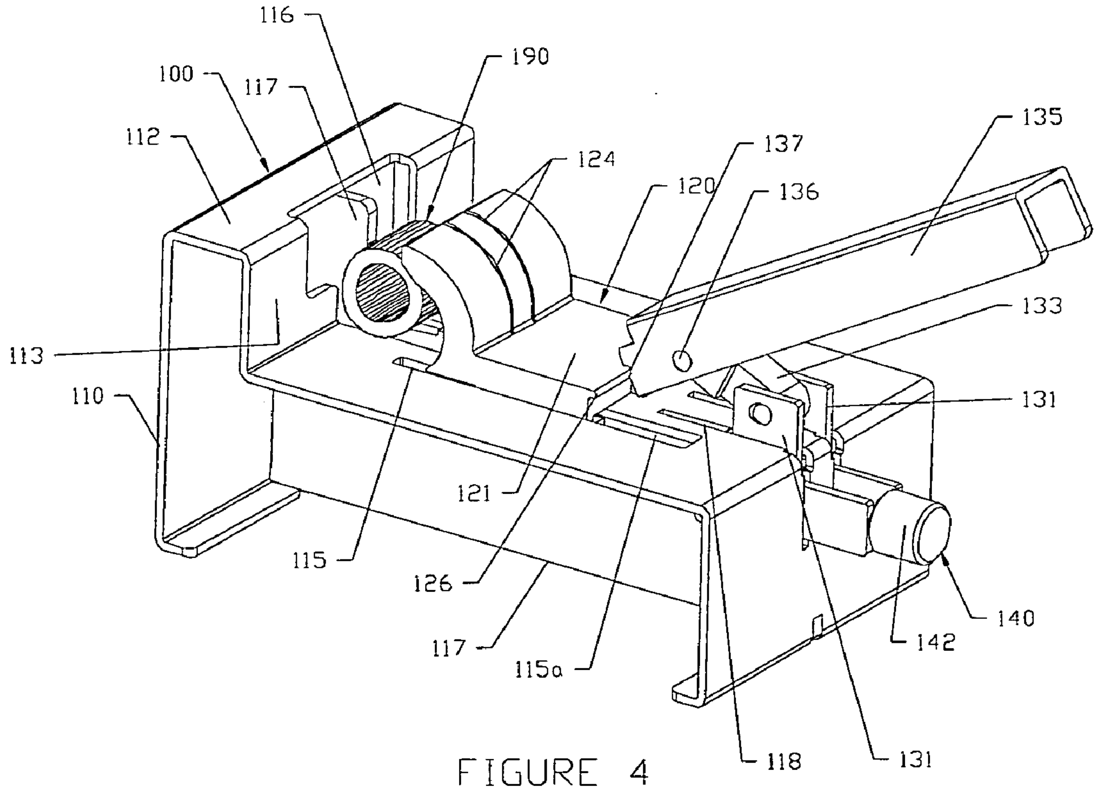
FIG. 4 depicts a perspective view of the cutting apparatus of the present invention holding a section of donor bone in an "open" position.

FIG. 4 depicts a perspective view of the cutting apparatus 100 of the present invention supporting a section of donor bone 190. Donor bone section 190 is beneficially placed on serrated surface 117*a*. In this configuration, donor bone section 190 is generally aligned with tracks 115. L-shaped track mounts 122 (not shown in FIG. 4) of blade guide 120 are inserted into openings 115*a* of tracks 115, so that blade guide 120 is slidably disposed within tracks 115 of base 110. Blade guide 120 can travel within tracks 115 along substantially planar surface 111 and can be selectively positioned along planar surface 111 of base 110 relative to serrated surface 117*a*(not shown in FIG. 4) and donor bone section 190.

Figure 5:
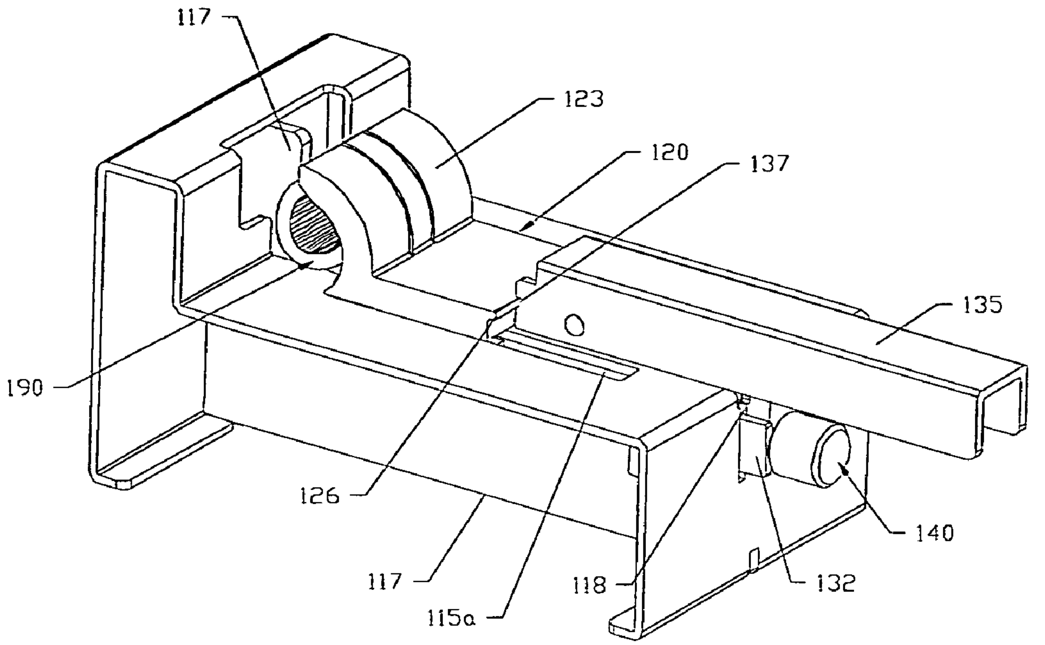
FIG. 5 depicts a perspective view of the cutting apparatus of the present invention holding a section of donor bone in a "closed" position.

Referring to FIG. 5, blade guide 120 is biased toward serrated surface 117*a* (and donor bone section 190 supported on said serrated surface 117*a*) and locked in place using adjustable lever-cam linkage 130. Yoke 131 is slidably disposed within slotted tracks 118 (partially obscured from view in FIG. 5) of base 110 to a desired position, and lever arm 135 is depressed. Slot 137 of lever arm 135 engages against lateral extension 126 of blade guide 120. Biasing bolt 140 can be screwed in or out, as desired, to act against lateral extensions 132 of yoke 131 in order to adjust the positioning of yoke 131. Donor bone section 190 is secured between bone holder 123 of blade guide 120 and serrated surface 117*a* of plate member 117. Said lever-cam linkage 130 allows for differences in size and geometry of a donor bone 190, as well as compression forces to be applied to such donor bone 190.

Figure 6:
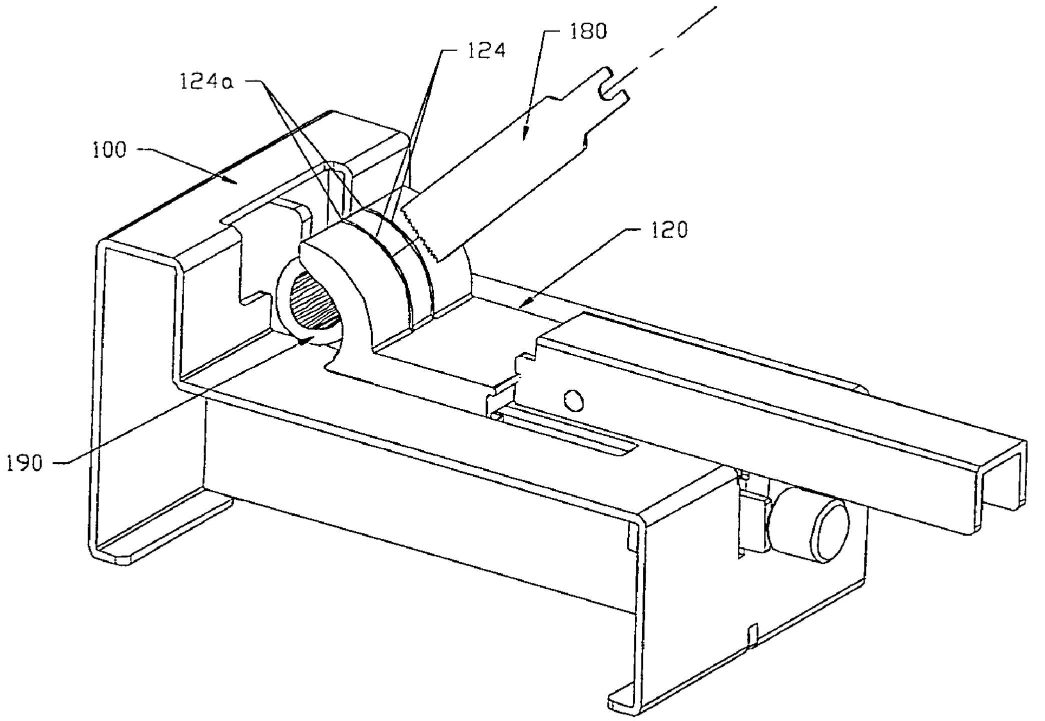
FIG. 6 depicts a perspective view of the cutting apparatus of the present invention holding a section of donor bone in a "closed" position during cutting operations.

FIG. 6 depicts a perspective view of cutting apparatus 100 of the present invention holding donor bone 190 in advance of the cutting process. Once donor bone section 190 is secured in place using the apparatus of the present invention as set forth in detail above, precision cuts can be made to donor bone section 190 in order to prepare bone grafts having desired shapes and sizes. Specifically, blade 180 is inserted through slots 124 of blade guide 120 to cut donor bone section 190. Slots 124 allow blade 180 (which can be any number of cutting devices known in the art such as, for example, a saggital saw blade) to move freely within a plane of radical oscillation. Slots 124, ideally having wider opening 124*a* at the leading edge of bone holder 123 to guide saw blade 180 into such slots 124, effectively guide the cutting edge of blade 180 through a donor bone section 190 within the desired plane. In one embodiment of the present invention, slots 124 are situated at fixed spacing intervals relative to one another, and at normal angles relative to the longitudinal axis of donor bone section 190.

Figure 7:
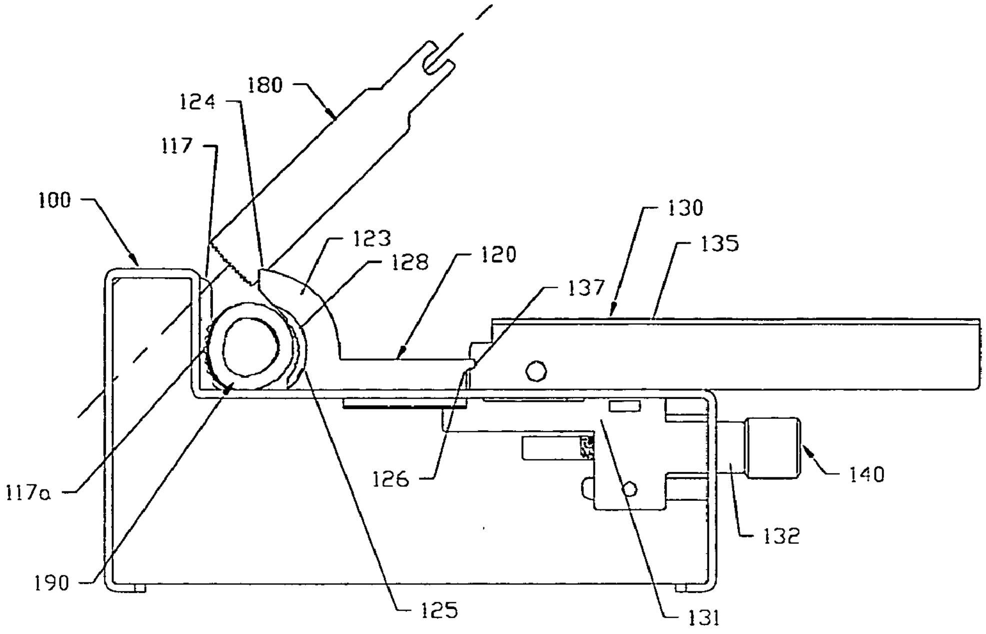
FIG. 7 depicts a side view of the cutting apparatus of the present invention holding a section of donor bone in a "closed" position.

FIG. 7 depicts a side view of cutting apparatus 100 of the present invention holding donor bone 190 during the cutting process. Blade guide 120 is biased toward serrated surface 117*a*, as well as donor bone section 190 supported on said serrated surface 117*a*, and locked in place using adjustable lever-cam linkage 130. Specifically, slot 137 of lever arm 135 engages against lateral extension 126 of blade guide 120 to bias said blade guide 120 toward donor bone section 190. Biasing bolt 140 can be screwed in or out, as desired, to act against lateral extensions 132 and adjust the positioning of yoke 131 relative to donor bone 190. Donor bone section 190 is secured between toothed protrusion 128 on curved inner surface 125 of bone holder 123, and serrated surface 117*a* of plate member 117. In FIG. 7, blade 180 is being inserted into a slot 124 of blade guide 120.

Figure 8:
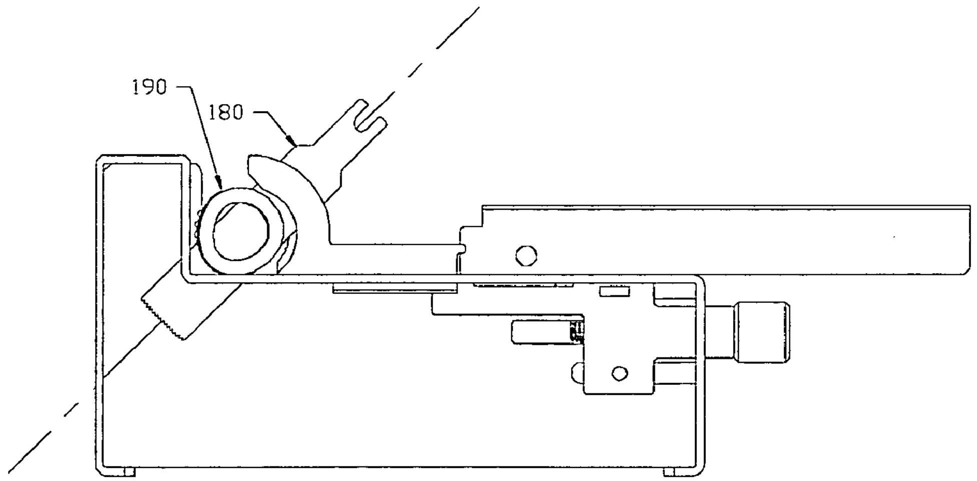
FIG. 8 depicts a side view of the cutting apparatus of the present invention holding a section of donor bone in a "closed" position during cutting operations.

FIG. 8 depicts the same general view as FIG. 7, except that blade 180 is inserted further into slot 124 of blade guide 120. As blade 180 exits donor bone section 190, blade 180 can extend freely into opening 116 of base 110 upon completion of a cut. Because multiple aligned slots 124 are formed in blade guide 120, two faces of a bone graft can be prepared without repositioning donor bone section 190.

Figure 9:
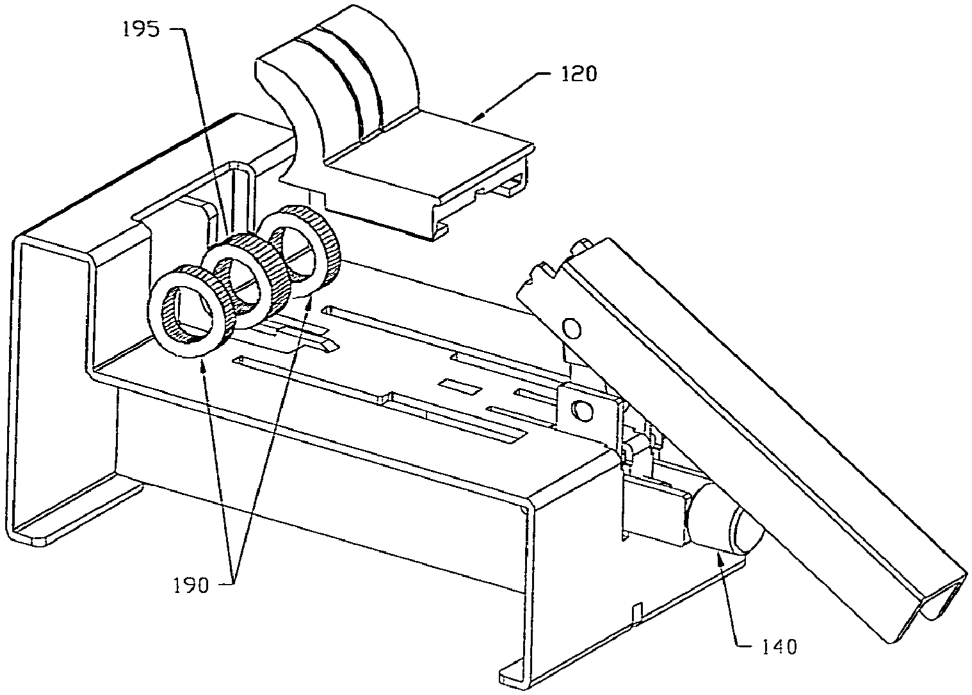
FIG. 9 depicts a perspective view of the cutting apparatus of the present invention following the cutting of a donor bone.

FIG. 9 depicts a perspective view of cutting apparatus 100 of the present invention following the cutting of donor bone section 190. Following such cutting operations, biasing bolt 140 is partially or fully unscrewed and blade guide 120 is removed from donor bone section 190. As depicted in FIG. 9, donor bone section 190 has been cut to form bone graft section 195, having a desired shape and size. Because cutting apparatus 100 of the present invention can securely hold donor bone section 190 during cutting operations, even when said cutting operations are relatively violent, bone graft section 195 can be cut to extremely thin dimensions without sacrificing cut quality. Such bone graft section 195 can be utilized in connection with any number of different beneficial medical procedures including, but not necessarily limited to, surgical procedures.

Figure 10:
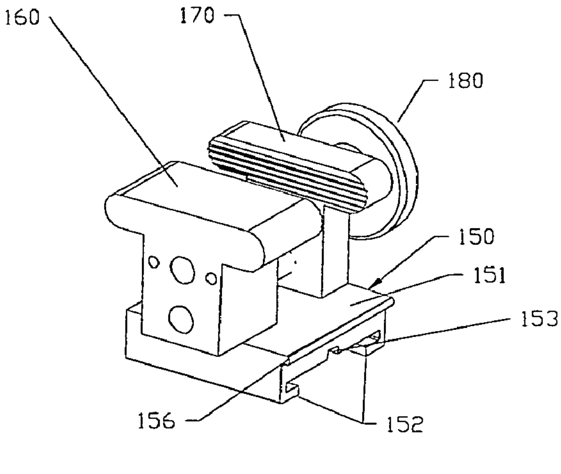
FIG. 10 depicts a perspective view of a finishing attachment of the present invention.

FIG. 10 depicts graft finishing attachment 150 that can be optionally utilized in connection with cutting apparatus 100 of the present invention. Graft finishing apparatus 150 comprises body section 151 and opposing vise members 160 and 170 which can be beneficially positioned relative to one another using biasing bolt 180. Opposing L-shaped track mounts 152 are disposed along the base of body section 151. Lateral extension 156 extends from one side of body section 151. Centering groove 153 mates with centering tab 117*b* (shown on FIG. 1).

Figure 11:
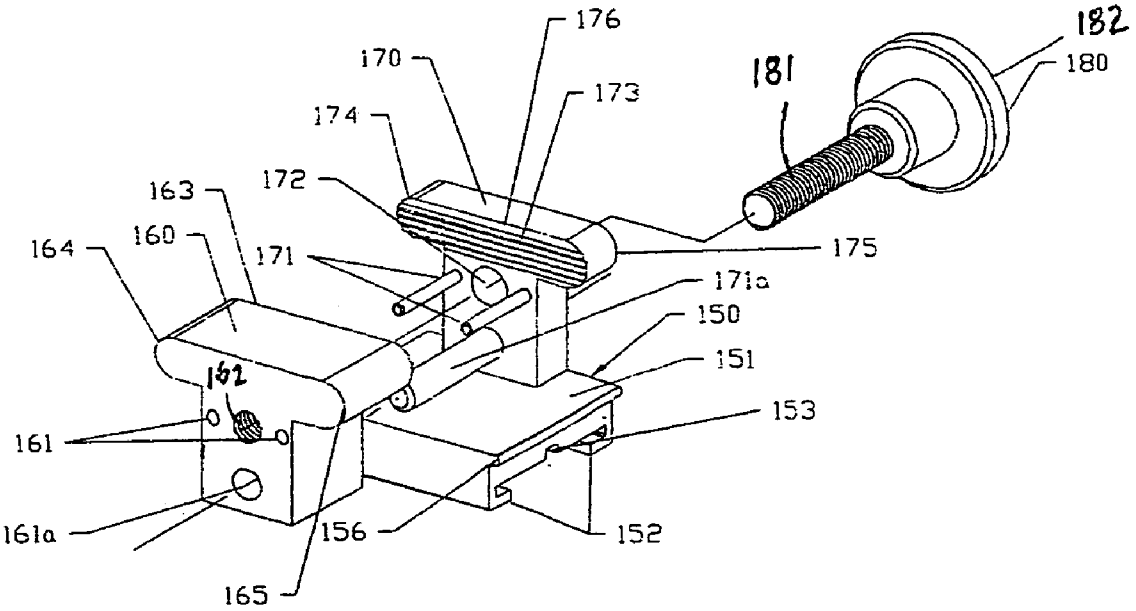
FIG. 11 depicts an exploded perspective view of a finishing attachment of the present invention.

FIG. 11 depicts an exploded view of graft finishing attachment 150 of the present invention. In the preferred embodiment, vise member 170 has a plurality of extensions 171 projecting from one side of vise member 170. Although said extensions 171 can take any number of different shapes, in the preferred embodiment said extensions 171 are cylindrical rods. Rods 171 are positioned to facilitate the placement of the maximum sized TLIF and PLIF grafts for finishing. Rod 171*a* is the main positioning pin for the movable jaw 160. Vise member also has bore 172, as well as serrated area 173. In the preferred embodiment, serrated area 173 also has rounded lateral members 174 and 175. A flat area 176 on the serrated area 173 provides a scale for the insertion of a bone ring for specific TLIF graft forming procedures.

Still referring to FIG. 11, vise member 160 has a plurality of smooth bores 161 for receiving extensions 171 of vise member 170. Vise member 160 also has threaded bore 162, as well as serrated area 163 (mostly obscured from view in FIG. 11). In the preferred embodiment, serrated area 163 also has rounded lateral members 164 and 165. Biasing bolt 180 having threaded section 181 and head 182 is disposed through aligned bores 172 and 162 of vise members 170 and 160, respectively. Biasing bolt 180 can be rotated to selectively move vise members 170 and 160 and, more particularly serrated areas 173 and 163, relative to one another. Also, in the preferred embodiment, the radii of curvature of rounded lateral members 174 and 164 are the same, while the radii of curvature of rounded lateral member 175 and 165 are the same.

Figure 12:
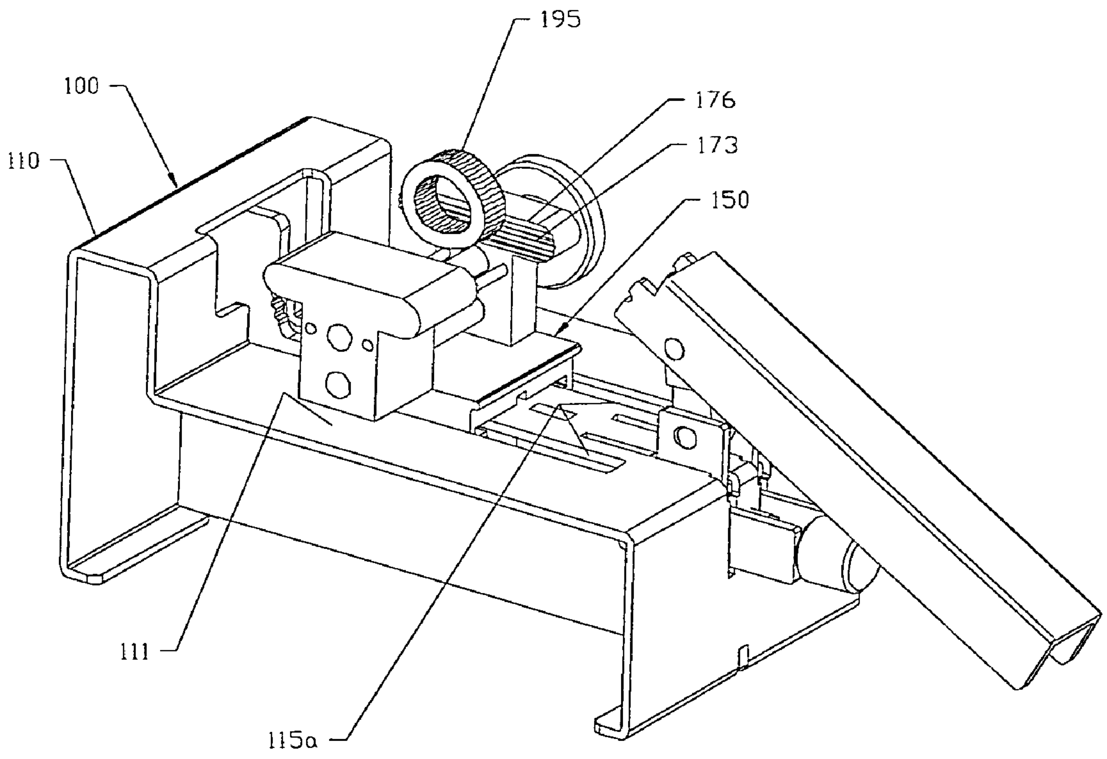
FIG. 12 depicts a perspective view of a section of donor bone prior to installation in the finishing attachment of the present invention.
Figure 13:
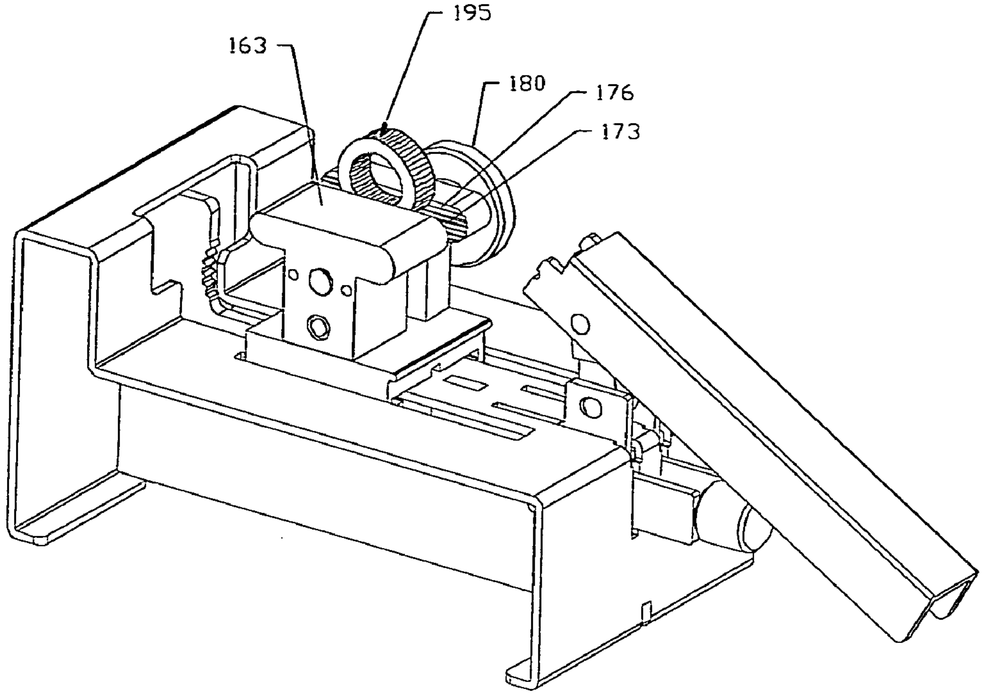
FIG. 13 depicts a perspective view of a section of donor bone installed in the finishing attachment of the present invention.

Referring to FIG. 12, blade guide 120 can be removed from slots 115 of base 110 and replaced with graft finishing attachment 150. Specifically, L-shaped track mounts 152 (partially obscured from view in FIG. 12) of graft finishing attachment 150 are inserted into openings 115*a* of tracks 115, so that graft finishing attachment is slidably disposed within tracks 115 of base 110 and can travel within tracks 115 along substantially planar surface 111. Biasing bolt 180 is rotated to separate vise members 170 and 160 and, more particularly serrated areas 173 and 163, from one another. Bone graft section 195 can be inserted within the gap between opposing serrated areas 173 and 163. Referring to FIG. 13, biasing bolt 180 can then be rotated to close the gap between opposing vise members 170 and 160, and thereby securely hold bone graft section 195 between serrated areas 173 and 163.

Figure 14:
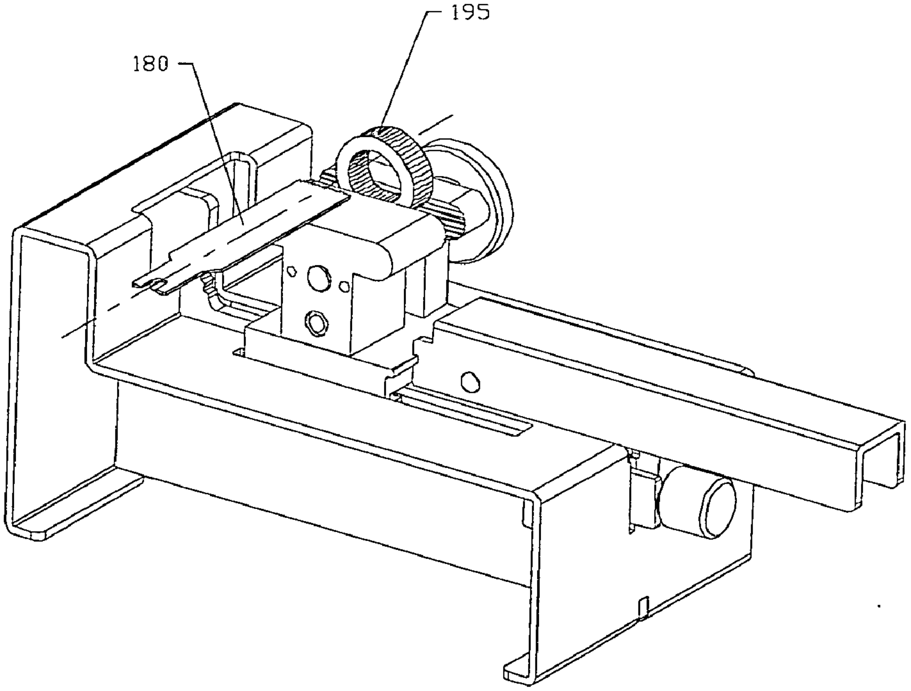
FIG. 14 depicts a perspective view of a section of donor bone installed in the finishing attachment of the present invention prior to cutting operations.
Figure 15:
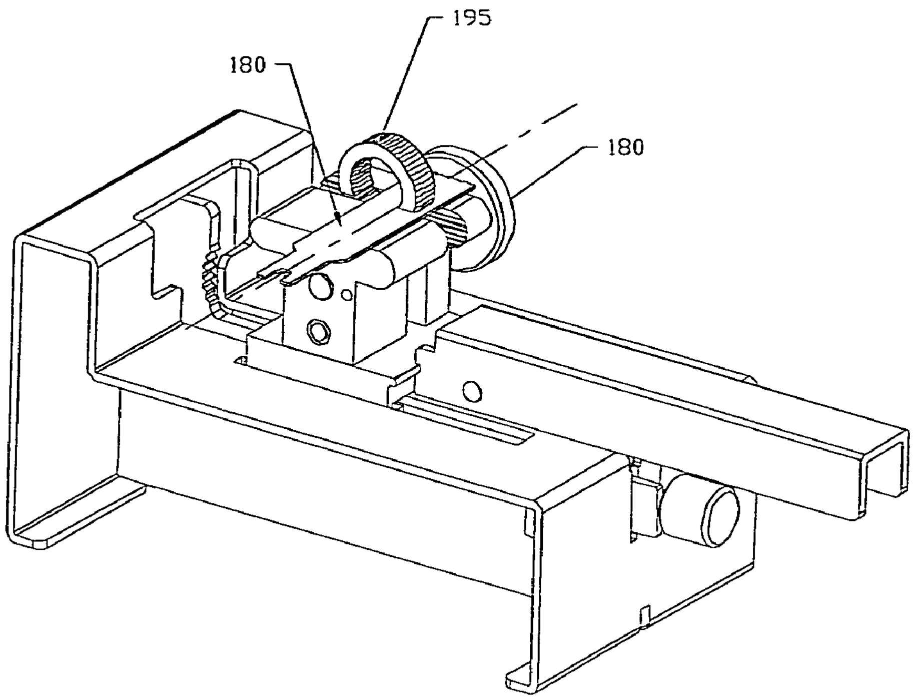
FIG. 15 depicts a perspective view of a section of donor bone installed in the finishing attachment of the present invention during cutting operations.
Figure 16:
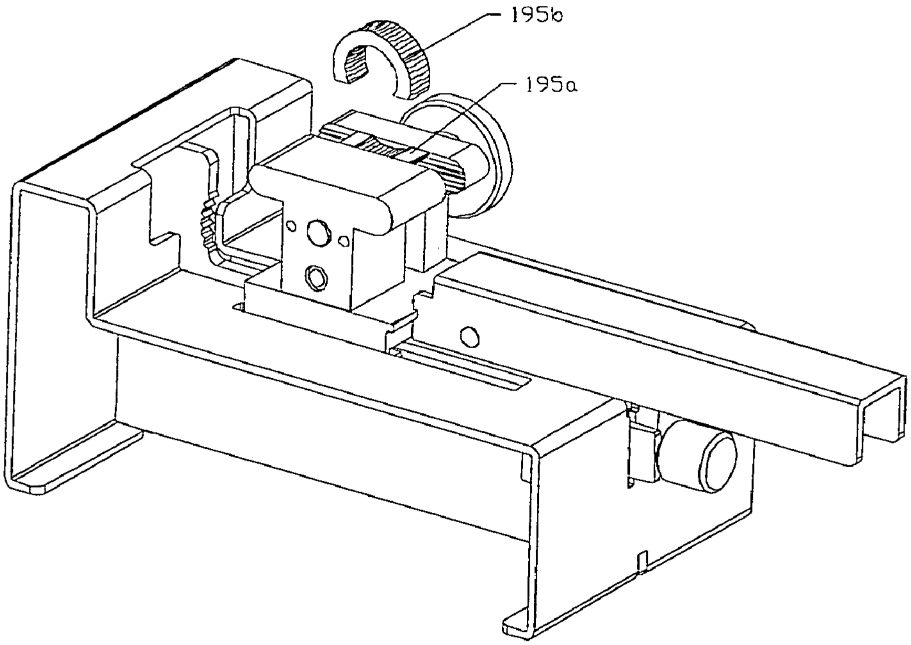
FIG. 16 depicts a perspective view of a section of donor bone installed in the finishing attachment of the present invention following cutting operations.

FIG. 14 depicts cutting operations on bone graft section 195 using graft finishing attachment 150. Graft finishing attachment 150 is positioned at the end of tracks 115 and locked in place using adjustable lever-cam linkage 130. Specifically, slot 137 of lever arm 135 engages against lateral extension 156 of graft finishing attachment 150 to secure said attachment within tracks 115. Bone graft section 195 is secured between opposing serrated areas 173 and 163. Blade 180, which can be any number of cutting devices known in the art such as, for example, a saggital saw blade is used to cut bone graft section 195 into a desired shape. To the extent that a horizontal cut is desired, the aligned upper surfaces of opposing vise members 170 and 160 can be used to guide such blade, as depicted in FIG. 15. Following such cutting operations, bone graft section 195 is further divided into graft section 195*a* and 195*b*.

Figure 17:
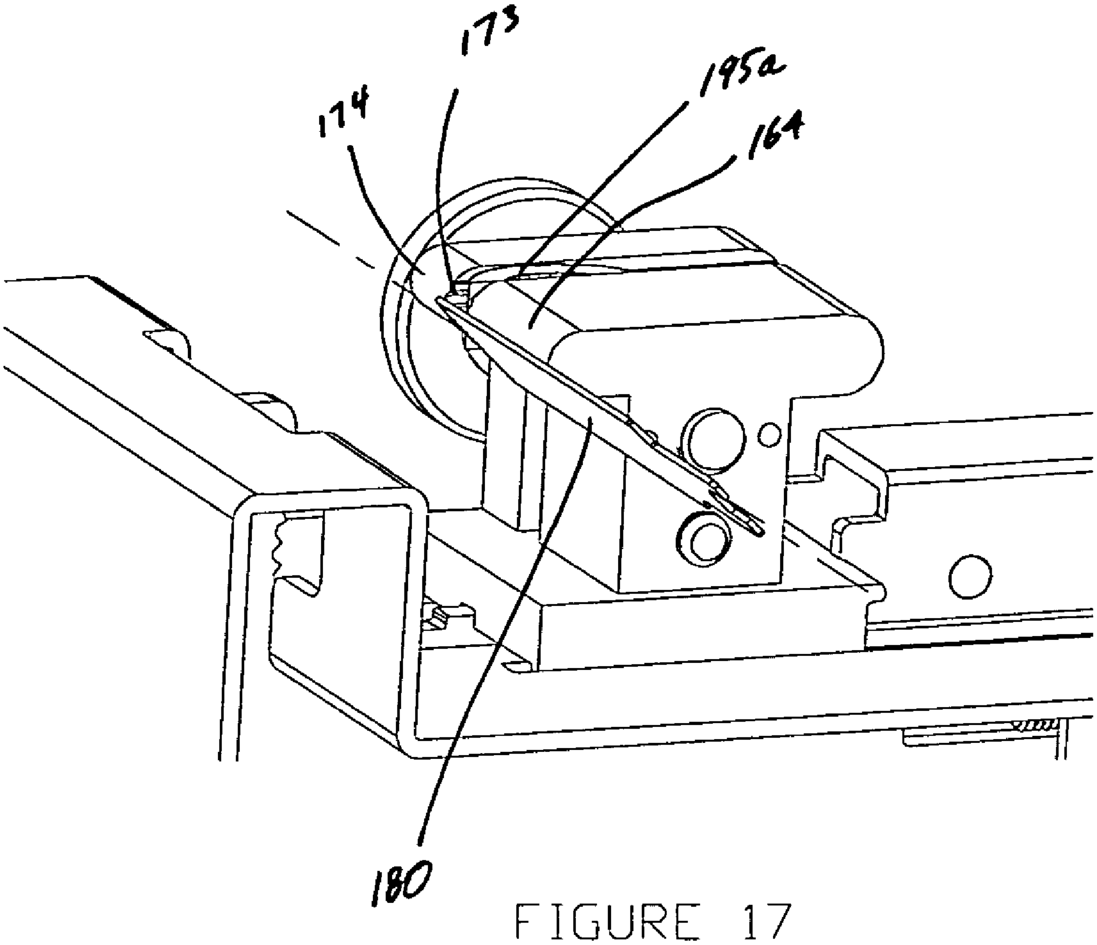
FIG. 17 depicts a perspective view of a bone graft being dressed off in the finishing attachment of the present invention.

Referring to FIG. 17, bone graft section 195*a* can be re-oriented and secured between opposing serrated areas 173 and 163 (not shown in FIG. 17). Blade 180 can be used to dress off or otherwise shape the edges of bone graft section 195*a*. If desired, aligned rounded lateral members 174 and 164 can be used as a guide for blade 180. Also, bone graft section 195*b* can also be finished in this manner and used to form a separate graft.

The above disclosed invention has a number of particular features which should preferably be employed in combination, although each is useful separately without departure from the scope of the invention. While the preferred embodiment of the present invention is shown and described herein, it will be understood that the invention may be embodied otherwise than herein specifically illustrated or described, and that certain changes in form and arrangement of parts and the specific manner of practicing the invention may be made within the underlying idea or principles of the invention.

What is claimed:

1. A method for forming bone grafts comprising:

a. placing an elongate donor bone having a longitudinal axis on a base having:

i. a substantially planar horizontal surface having a first end and a second end;

ii. an upright member extending along said first end of said substantially planar horizontal surface, wherein said upright member defines a substantially planar vertical surface having an opening, and said vertical surface is oriented substantially perpendicular to said substantially planar horizontal surface;

iii. a vertical plate member having a serrated edge for supporting said donor bone, wherein said serrated edge extends through said opening of said substantially planar vertical surface and is oriented substantially normal to the longitudinal axis of said donor bone; and iv. a blade guide slidably disposed on said substantially planar horizontal surface of said base having a plurality of substantially vertical slots extending through said blade guide, wherein a first slot is situated on one side of said serrated edge of said vertical plate member, a second slot is situated on the opposite side of said serrated edge of said vertical plate member, and said serrated edge of said vertical plate member is disposed between said first and second slots;

b. biasing said blade guide toward said donor bone to secure said donor bone between said blade guide and said vertical plate member;

c. passing a blade through said first slot extending through said blade guide to cut said donor bone on one side of said vertical plate member; and d. passing said blade through said second slot extending through said blade guide to cut said donor bone on the opposite side of said vertical plate member from said first slot.

2. The method of claim 1, wherein said blade guide has a curved surface facing said donor bone.

* * * * *